United States Patent [19]

Teulon et al.

[11] Patent Number: 4,668,801
[45] Date of Patent: May 26, 1987

[54] 1-(2-CARBOALKOXY 4-(THIENYL-ALKYL-AMIDO) PHENYOXYL 30 AMINO 20 PROPANOLS, THEIR PREPARATION AND APPLICATIONS THEREOF IN THERAPEUTICS

[75] Inventors: Jean M. Teulon, La Celle Saint Cloud; Etienne Bouley, Courbevoie, both of France

[73] Assignee: Carpibem (Centre d'activite et de recherche Pharmaceutiou et Industrielee Biologique), Malmaison, France

[21] Appl. No.: 814,077

[22] Filed: Dec. 23, 1985

Related U.S. Application Data

[63] Continuation of Ser. No. 511,179, Jul. 6, 1983, abandoned.

[30] Foreign Application Priority Data

Jul. 16, 1982 [FR] France .............................. 82 12499
Jun. 6, 1983 [FR] France .............................. 83 09361

[51] Int. Cl.$^4$ ..................... C07D 333/22; A61K 31/38
[52] U.S. Cl. ........................................................ 549/72
[58] Field of Search ..................................... 549/72, 77

[56] References Cited

U.S. PATENT DOCUMENTS 3,562,297  2/1971  Howe et al. ........................ 549/72

FOREIGN PATENT DOCUMENTS

A1543689  3/1973  France .
A2291741  6/1976  France .
A245854   8/1976  France .
8301772   5/1983  PCT Int'l Appl. ................... 549/72

*Primary Examiner*—Alan Siegel
*Attorney, Agent, or Firm*—Morgan & Finnegan

[57] ABSTRACT

The invention relates to new compounds of formula:

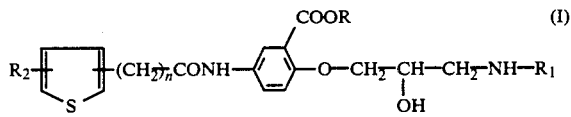

$R_2$ = H, alkyl, halogen, cycle joined to the thiophene; n = 0 or 1.

β-blocking properties comparable to those of propranolol and/or diuretic properties comparable to those of thiazidic substances.

6 Claims, No Drawings

1-(2-CARBOALKOXY 4-(THIENYL-ALKYL-AMIDO) PHENYOXYL 30 AMINO 20 PROPANOLS, THEIR PREPARATION AND APPLICATIONS THEREOF IN THERAPEUTICS

This application is a continuation of application Ser. No. 511,179, filed July 6, 1983 now abandoned.

The present invention relates as new products to the compounds of general formula I hereinbelow and to their acid addition salts. The compounds in question present a very original pharmacological profile insofar as they are endowed with β-blocking properties comparable to those of propranolol and/or with diuretic properties comparable to those of thiazidic substances. The present invention also relates to the process for preparing said products and to the applications thereof in therapeutics. It further relates to the new intermediary compounds allowing synthesis of said products.

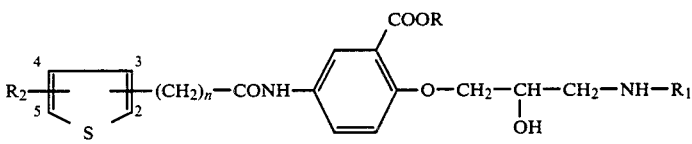

In formula I,

R represents an alkyl radical of 1 to 5 carbon atoms, branched or not, advantageously the ethyl radical;

$R_1$ is an alkyl radical of 1 to 5 carbon atoms, straight or branched and, advantageously, $R_1$ is the isopropyl radical or the terbutyl radical;

$R_2$ may be H, an alkyl radical of 1 to 5 carbon atoms, straight, branched or cyclic, or a halogen and $R_2$ may also designate a cycle joined to the thiophene, such as cyclohexyl or cyclopentyl for example, $R_2$ advantageously designating H or the methyl group;

n=0 or 1.

The compounds according to the invention are synthesized by action of a base $NH_2$—$R_1$ ($R_1$ being defined as hereinabove) on a compound of formula II, without solvent or in a conventional organic solvent such as alcohols, at a temperature of between 20° C. and 150° C.

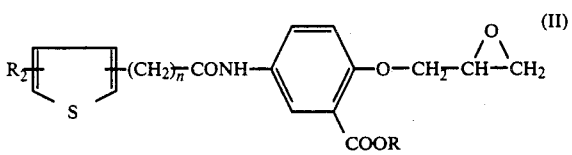

($R_2$, R and n being as defined hereinabove).

The compounds of formula II may generally be obtained by reacting a phenol of general formula III with an epihalohydrin, particularly epichlorohydrin or epibromohydrin. The phenol of formula III is previously metalled by conventional metallation agents such as sodium hydroxide, potassium hydroxide, an alcoholate or sodium hydride, etc.. in a dilute alcoholic, alcoholic medium or in a solvent such as DMF, at a temperature of between 20° C. and 150° C.

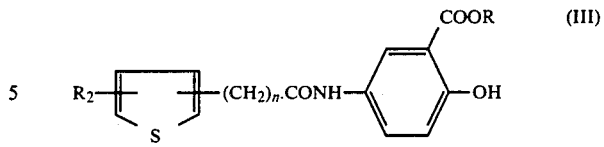

($R_2$, R and n being as defined hereinabove).

These processes of synthesis, known per se, yield poorly defined compounds with low outputs. Applicants have discovered and developed a new process consisting in reacting the phenol of formula III with an excess of epichlorohydrin in the presence of a catalyst, such as benzyltrimethylammonium chloride, at a temperature ranging from 110° C. to 130° C. This process yields perfectly defined crystallized compounds with good outputs.

The compounds of formula III are obtained by a conventional method consisting in reacting the acid chloride of the corresponding thienyl carboxylic acid on a 4-amino 2-carbalkoxy phenol, in the presence of a base such as triethylamine, in a solvent such as acetone or benzene.

The non-toxic addition salts of the compounds of formula I may be obtained by reacting these compounds with an inorganic or organic acid according to a method known per se. Among the acids which may be used to this end, mention will be made of hydrochloric, hydrobromic, sulphuric, phosphoric, 4-toluenesulfonic, methane-sulfonic, cyclohexylsulfamic, oxalic, succinic, formic, maleic, aspartic, cinnamic, glutamic, N-acetylaspartic, N-acetylglutamic, ascorbic, malic, fumaric, lactic and benzoic acids.

The new compounds according to the invention possess remarkable pharmacological properties and may be used in therapeutics as β-blockers of propranolol type and/or as diuretics of thiazidic type, since, unexpectedly, they may present these two properties simultaneously, for the treatment of hypertension. These products are also virtually non-toxic and cardioselective.

A particularly preferred sub-family IA of the compound according to the invention corresponds to formula (I) in which the carboxamide chain is directly bonded to the thiophene cycle (n=0) and in 2 position of this cycle. The compounds of this family present in fact excellent diuretic and β-blocking properties simultaneously.

It will further be noted that the sub-family IB characterized by [n=0, carboxamide chain in position 3] corresponds to products associating a good β-blocking activity with a diuretic tendency.

Finally, the sub-families IC [n=1, chain in 2 position of the thiophene] and ID ]n=1, chain in 3 position of the thiophene] correspond to non-diuretic β-blocking products.

Furthermore, it has been observed that the compounds according to the invention in which $R_2$ represents H or 4-methyl are particularly interesting. These products are particularly superior to a 5-methyl substitution on the thiophene.

The particular interest of the compounds IE in which, simultaneously: n=0, the carboxamido chain is in 2 position of the thiophene, and $R_2$=H or 4-methyl, will therefore have been noted.

In human therapeutics, the compounds of formula I and their non-toxic acid addition salts may be administered in particular by the oral route. The use of capsules or tablets containing from 50 to 300 mg of active ingredient in association with a physiologically acceptable excipient is recommended. The compounds claimed present the advantage of rendering treatment simpler. Furthermore, with respect to the β-blocker/diuretic associations used in the treatment of hypertension, the compounds of formula IA have the decisive advantage of unique pharmacokinetics. As other examples of possible indications, angor pectoris, arrhythmia, migraines will be mentioned.

Further characteristics and advantages of the invention will be more readily understood on reading some non-limiting examples of preparation given by way of illustration. The corresponding formulae are presented in the single Table hereinbelow.

EXAMPLE 1

1-[2-carbethoxy 4-(5-methyl 2-thiophene carboxamido)phenoxy]2,3-epoxy propane

Formula II: $R=C_2H_5$, $R_2=CH_3$ in 5, n=0.

In a flask, the mixture of 35 g of 2-carbethoxy 4-(5-methyl-2-thiophene carboxamido)phenol and 175 ml of epichlorohydrin, is heated to 110° C., then 2.9 g of benzyltrimethylammonium chloride are introduced. The reaction mixture is then heated to reflux for 30 mins., then cooled. Once the temperature of the medium has dropped again to 50° C., 200 ml of water are added and the mixture is stirred strongly. After decantation, the aqueous phase is extracted twice with ether and the organic phases are dried over magnesium sulfate, filtered and concentrated in vacuo. The residue hardens in ether. After three washings in 50 ml of isopropylic ether, 30 g of 1-[2-carbethoxy 4-(5-methyl 2-thiophene carboxamido)phenoxy]2,3-epoxy propane are obtained in the form of white crystals melting at 109° C.

EXAMPLE 2

1-[2-carbethoxy 4-(5-methyl 2-thiophene carboxamide)phenoxy]3-terbutylamino 2-propanol Formula I: $R=C_2H_5$, $R_1=$

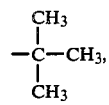

$R_2=CH_3$ in 5, n=0.

In a flask, 14 g of the epoxide prepared in Example 1, in 30 ml of terbutylamine and 100 ml of ethanol, are heated to reflux for 8 hours. The alcoholic solution is then concentrated in vacuo and the residue taken up in 150 ml of water, 5 ml of glacial acetic acid and 100 ml of isopropyl acetate. The organic phase is eliminated by decantation and the acid aqueous phase is neutralized by a solution of ammonia, then extracted twice with 50 ml of chloroform. After drying over magnesium sulfate, the chloroform phase is filtered and concentrated in vacuo. The oil obtained is taken up in isopropyl acetate hot. The solution is filtered hot then cooled. The product obtained by precipitation is washed abundantly with ether. Finally, 4 g of 1-[2-carbethoxy 4-(5-methyl 2-thiophene carboxamido)phenoxy]3-terbutylamino 2-propanol in the form of white crystals melting at 110° C., are obtained.

EXAMPLE 3

1-[2-carbethoxy 4-(5-methyl 2-thiophene carboxamido)phenoxy]3-isopropylamino 2-propanol Formula I: $R=C_2H_5$, $R_1=$

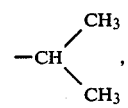

$R_2=CH_3$ in 5, n=0.

The modus operandi is identical to that described in Example 2, but replacing the terbutylamine by isopropylamine. Finally, a residue is obtained which, recrystallized from ethyl acetate, yields 6 g of 1-[2-carbethoxy 4-(5-methyl 2-thiophene carboxamido)phenoxy]3-isopropylamino 2-propanol in the form of white crystals melting at 121° C.

EXAMPLE 4

1-[2-carbethoxy 4-(5-chloro 2-thiophene carboxamido)phenoxy]2,3-epoxy propane

Formula II: $R=C_2H_5$, $R_2=Cl$ in 5, n=0.

With the same modus operandi as described in Example 1, but by using 11 g of 2-carbethoxy 4-(5-chloro 2-thiophene carboxamido)phenol, 60 ml of epichlorohydrin and 1 g of benzyltrimethylammonium chloride, 7 g of an oil which does not crystallize and which is used as such, are obtained.

EXAMPLE 5

Hydrochloride of 1-[2-carbethoxy 4-(5-chloro 2-thiophene carboxamido)phenoxy]3-terbutylamino 2-propanol Formula I: $R=C_2H_5$, $R_1=$

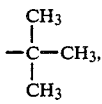

$R_2=Cl$ in 5, n=0.

The oil obtained in Example 4 is dissolved in 50 ml of terbutylamine and the mixture taken to reflux for 8 hours. The modus operandi is then the same as that described in Example 2. The crystals are obtained which are taken up in 100 ml of acetone to which are added 10 ml of an ethereal solution of hydrochloric acid. After filtration of the precipitate and washing with acetone, then with ether, 700 mg of hydrochloride of 1-[2-carbethoxy 4-(5-chloro 2-thiophene carboxamido)phenoxy]3-tertbutylamino 2-propanol are obtained in the form of white crystals melting at 165° C.

EXAMPLE 6

1-[2-carbethoxy 4-(4-methyl 2-thiophene carboxamido)phenoxy]2,3-epoxy propane

Formula II: $R=C_2H_5$, $R_2=CH_3$ in 4, n=0.

The modus operandi is identical to that described in Example 1. By using 30 g of 2-carbethoxy 4-(4-methyl 2-thiophene carboxamido)phenol, 3 g of benzyl trimethylammonium chloride and 150 ml of epichlorohydrin, an oil is obtained, after treatment, which is extracted twice with 100 ml of ether. After drying of the ethereal phase and concentration in vacuo, 12 g of 1-[2-carbethoxy 4-(4-methyl 2-thiophene carboxamido)phenoxy]2,3-epoxy propane are obtained in the form of white crystals melting at 118° C.

EXAMPLE 7

Hydrochloride of 1-[2-carbethoxy 4-(4-methyl 2-thiophene carboxamido)phenoxy]3-terbutylamino 2-propanol Formula I: $R=C_2H_5$, $R_1=$

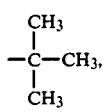

$R_2=CH_3$ in 4, $n=0$.

The modus operandi is identical to that described in Example 2. From 10 g of the epoxide prepared in Example 6 and 50 ml of terbutylamine, 6 g of crystals are obtained which are dissolved in the minimum of ethanol. An ethereal solution of hydrochloric acid is then poured until pH~1 is obtained and the precipitate is collected by filtration. Recrystallization from ethanol yields 3.3 g of hydrochloride of 1-[2-carbethoxy 4-(4-methyl 2-thiophene carboxamido)phenoxy]3-terbutylamino 2-propanol in the form of white crystals melting at 186° C.

EXAMPLE 8

1-[2-carbethoxy 4-[2-(4,5,6,7-tetrahydro)thianaphthene carboxamido]phenoxy]2,3-epoxy propane Formula II: $R=C_2H_5$, $R_2=$

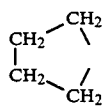

in 4,5, $n=0$.

In the same way, from the 2-carbethoxy 4-[2-(4,5,6,7-tetrahydro)thianaphthene carboxyamido]phenol of chloride of benzyltrimethylammonium and of epichlorohydrin, 1-[2-carbethoxy 4-[2-(4,5,6,7-tetrahydro)thianaphthene carboxamido]phenoxy]2,3-epoxy propane is obtained.

EXAMPLE 9

1-[2-carbethoxy 4-[2-(4,5,6,7-tetrahydro)thianaphthene carboxamido]phenoxy]3-terbutylamino 2-propanol Formula I: $R=C_2H_5$, $R_1=$

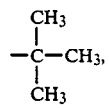

$R_2=$

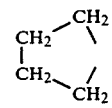

in 3,4, $n=0$.

By operating in accordance with the modus operandi described in Example 2, but from the epoxide obtained in Example 8 and from terbutylamino, 1-[2-carbethoxy 4-[2-(4,5,6,7-tetrahydro)thianaphthene carboxamido]phenoxy]3-terbutylamino 2-propanol is obtained.

EXAMPLE 10

1-[2-carbethoxy 4-(2-thienyl carboxamido)phenoxy]2,3-epoxy propane

Formula II: amide in 2, $n=0$, $R=C_2H_5$.

In a flask, the mixture of 10 g of 4-(2-thienyl carboxamido)2-carbethoxy phenol and 60 ml of epichlorohydrin is heated to 110° C. then 0.9 g of benzyltrimethylammonium chloride are added. The mixture is then heated to reflux for ½ hr. then cooled. Once the temperature has dropped again to 50° C., 150 ml of water are introduced. The reaction mixture is stirred, then extracted twice with 50 ml of ether. The ethereal phases are dried and evaporated to dryness. The residue obtained crystallizes from ether and thus yields 8 g of 1-[2-carbethoxy 4-(2-thienyl carboxamido)phenoxy]2,3-epoxy propane melting at 110° C.

EXAMPLE 11

1-[2-carbethoxy 4-(3-thienyl carboxamido)phenoxy]2,3-epoxy propane

Formula II: amide in 3, $n=0$, $R=C_2H_5$.

According to the modus operandi described in Example 1 but from 13 g of 4-(3-thienyl carboxamido)2-carbethoxy phenol, 70 ml of epichlorohydrin and 1 g of benzyltrimethylammonium chloride, 8 g of 1-[2-carbethoxy 4-(2-thienyl carboxamido)phenoxy]2,3-epoxy propane melting at 119° C. are obtained.

EXAMPLE 12

1-[2-carbethoxy 4-(2-thienyl carboxamido)phenoxy]3-isopropyl amino 2-propanol (base)

Formula I: amide in 2, $n=0$, $R=C_2H_5$, $R_1=$

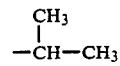

In a flask, with stirring, 8 g of the epoxide prepared in Example 1 and 10 ml of isopropylamine in 50 ml of ethanol are heated to 50° C. After 8 hrs. of heating at 50° C., the alcoholic solution is concentrated in vacuo and the residue taken up in a mixture of 100 ml of isopropyl acetate and 200 ml of water. Cold, 3 ml of glacial acetic acid are then added, and the mixture is stirred until a limpid medium is obtained. The isopropyl acetate is then eliminated by decantation and the acetic solution rendered basic by ammonia cold. The basic phase is extracted twice with 50 ml of chloroform. After drying and concentration in vacuo of the organic phase, a pasty residue is obtained which crystallizes from 50 ml of ether to yield 4.5 g of 1-[2-carbethoxy 4-(2-thienyl carboxamido)phenoxy]3-isopropylamino 2-propanol melting at 108° C.

EXAMPLE 13

1-[2-carbethoxy 4-(2-thienyl carboxamido)phenoxy]3-terbutyl amino 2-propanol (base)

Formula I: amide in 2, n=0, R=C$_2$H$_5$, R$_1$=

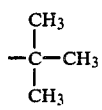

According to the modus operandi of Example 3 but from 8 g of epoxide described in Example 1 and 10 ml of terbutylamine, 3.5 g of 1-[2-carbethoxy 4-(2-thienyl carboxamido)phenoxy]3-terbutyl-amino 2-propanol melting at 125° C. are obtained.

EXAMPLE 14

1-[2-carbethoxy 4-(3-thienyl carboxamido)phenoxy]3-isopropyl amino 2-propanol (base)

Formula I: amide in 3, n=0, R=C$_2$H$_5$, R$_1$=

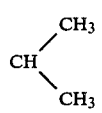

According to the modus operandi of Example 3 but from 8 g of the epoxide prepared in Example 2, 5.5 g of 1-[2-carbethoxy 4-(3-thienyl carboxamido)phenoxy]3-isopropylamino 2-propanol melting at 132° C. are obtained.

EXAMPLE 15

1-[2-carbethoxy 4-(3-thienyl carboxamido)phenoxy]3-terbutylamino 2-propanol (base)

Formula I: amide in 3, n=0, R=C$_2$H$_5$, R$_1$=

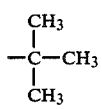

According to the modus operandi of Example 4 but from 5.6 g of epoxide prepared in Example 2, 3.5 g of 1-[2-carbethoxy 4-(3-thienyl carboxamido)phenoxy]3-terbutylamino 2-propanol melting at 126° C. are obtained.

EXAMPLE 16

1-[2-carbethoxy 4-(2-thienyl acetamido)phenoxy]2,3-epoxy propane

Formula II: amide in 2, n=1, R=C$_2$H$_5$.

According to the modus operandi described in Example 1 but from 19.3 g of 2-carbethoxy 4-(2-thienyl acetamido)phenol and 1.9 g of benzyltrimethylammonium chloride, 22.5 g of an oil which is used crude for the following syntheses are obtained.

EXAMPLE 17

1-[2-carbethoxy 4-(2-thienyl acetamido)phenoxy]3-terbutylamino 2-propanol (base)

Formula I: amide in 2, n=1, R=C$_2$H$_5$, R$_1$=

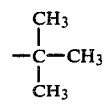

According to the modus operandi described in Example 3 but from 11.5 g of epoxide obtained in Example 7 and 50 ml of terbutylamine, 3.5 g of 1-[2-carbethoxy 4-(2-thienyl acetamido)phenoxy]3-terbutylamino 2-propanol melting at 118° C. are obtained.

EXAMPLE 18

1-[2-carbethoxy 4-(3-thienyl acetamido)phenoxy]2,3-epoxy propane Formula II: amide in 3, n=1, R=C$_2$H$_5$.

According to the modus operandi described in Example 1 but from 27.4 g of 2-carbethoxy 4-(3-thienyl acetamido)phenol and 2.7 g of benzyltrimethylammonium chloride, 30 g of an oil which is employed as such for subsequent use are obtained.

EXAMPLE 19

1-[2-carbethoxy 4-(3-thienyl acetamido)phenoxy]3-terbutylamino 2-propanol

Formula I: amide in 3, n=1, R=C$_2$H$_5$ R$_1$=

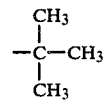

According to the modus operandi described in Example 3 but from 15 g of the epoxide obtained in Example 9 and 50 ml of terbutylamine, 2.8 g of 1-[2-carbethoxy 4-(3-thienyl acetamido)phenoxy]3-terbutylamino 2-propanol melting at 117° C. are obtained.

EXAMPLE 20

1-[2-carbethoxy 4-(3-thienyl acetamido)phenoxy]3-ispropyl amino 2-propanol (base)

Formula I: amide in 3, n=1, R=C$_2$H$_5$, R$_1$=

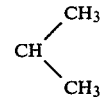

According to the modus operandi of Example 3 but from 12.5 g of the epoxide obtained in Example 9 and 50 ml of isopropylamine, 3.5 g of 1-[2-carbethoxy 4-(3-thienyl acetamido)phenoxy]3isopropylamino 2-propanol melting at 130° C. are obtained.

EXAMPLE 21

1-[2-carbomethoxy 4-(2-thienyl carboxamido)phenoxy]2,3-epoxy propane

Formula II: amide in 2, n=0, R=CH$_3$.

According to the modus operandi of Example 1 but from 35 g of 2-carbomethoxy 4-(2-thienyl carboxamido)phenol, 210 ml of epichlorohydrin and 3 g of benzyltrimethylammonium chloride, there are obtained, after recrystallization of the crude oil from isopropyl acetate, 17 g of 1-[2-carbomethoxy 4-(2-thienyl carboxamido)phenoxy]2,3-epoxy propane melting at 131° C.

EXAMPLE 22

1-[2-carbomethoxy 4-(2-thienyl carboxamido)phenoxy]3-terbutylamino 2-propanol (base)

Formula I: amide in 2, n=0, R=CH$_3$, R$_1$=

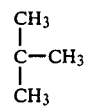

According to the modus operandi described in Example 3 but from 3.6 g of the epoxide described in Example 12 and 10 ml of terbutylamine, 1 g of 1-[2-carbomethoxy 4-(2-thienyl carboxamido)phenoxy]3-terbutylamino 2-propanol melting at 136° C. is obtained.

TABLE

| | | References |
|---|---|---|
| Example 1 | CH$_3$-thienyl-CONH-phenyl(COOC$_2$H$_5$)-OCH$_2$CH—CH$_2$(O epoxide) | |
| Example 2 | CH$_3$-thienyl-CONH-phenyl(COOC$_2$H$_5$)-OCH$_2$CHCH$_2$NH—C(CH$_3$)$_3$, OH | 788-56 |
| Example 3 | CH$_3$-thienyl-CONH-phenyl(COOC$_2$H$_5$)-OCH$_2$CHCH$_2$NH—CH(CH$_3$)$_2$, OH | 788-57 |
| Example 4 | Cl-thienyl-CONH-phenyl(COOC$_2$H$_5$)-OCH$_2$CH—CH$_2$(O epoxide) | |
| Example 5 | Cl-thienyl-CONH-phenyl(COOC$_2$H$_5$)-OCH$_2$CHCH$_2$NH—C(CH$_3$)$_3$, OH, HCl | 788-58 |
| Example 6 | CH$_3$-thienyl-CONH-phenyl(COOC$_2$H$_5$)-OCH$_2$CH—CH$_2$(O epoxide) | |
| Example 7 | CH$_3$-thienyl-CONH-phenyl(COOC$_2$H$_5$)-OCH$_2$CHCH$_2$NH—C(CH$_3$)$_3$, OH, HCl | 788-59 |
| Example 8 | tetrahydrobenzothienyl-CONH-phenyl(COOC$_2$H$_5$)-OCH$_2$CH—CH$_2$(O epoxide) | |
| Example 9 | tetrahydrobenzothienyl-CONH-phenyl(COOC$_2$H$_5$)-OCH$_2$CHCH$_2$NH—C(CH$_3$)$_3$, OH | |

TABLE -continued
| | | References |
|---|---|---|
| Example 10: | 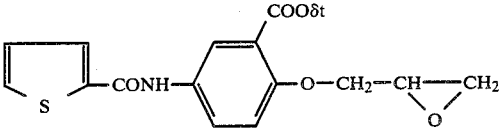 | |
| Example 11: | 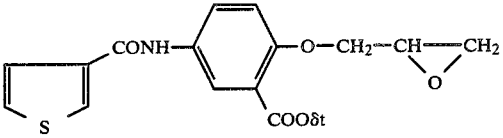 | |
| Example 12: | 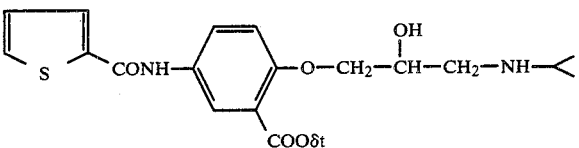 | 788-43 |
| Example 13: | 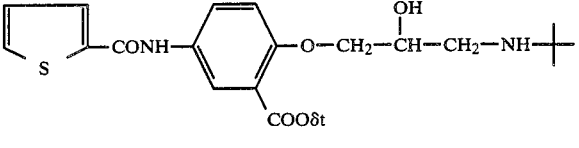 | 788-42 |
| Example 14: | 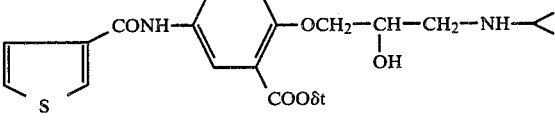 | 5130-04 |
| Example 15: | 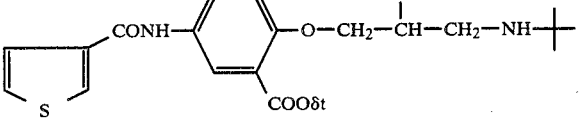 | 5130-01 |
| Example 16: | 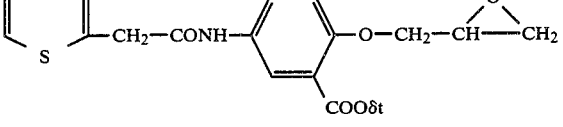 | |
| Example 17: | 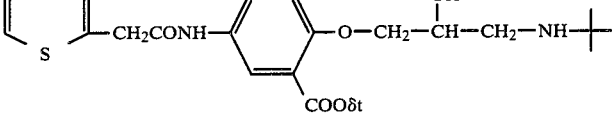 | 5130-02 |
| Example 18: | 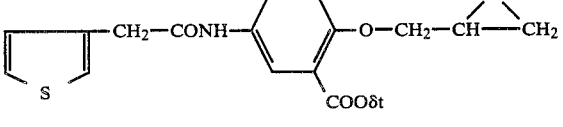 | |
| Example 19: | 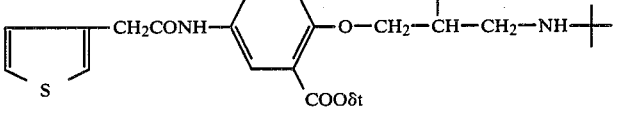 | 5130-03 |

TABLE -continued

Example 20:

[Structure: thiophene-CH2CONH-phenyl(COOEt)-O-CH2-CH(OH)-CH2-NH-C(CH3)3]

Example 21:

[Structure: thiophene-CO-NH-phenyl(COOCH3)-OCH2CH(epoxide)CH2]

Example 22: 788-48

[Structure: thiophene-CONH-phenyl(COOCH3)-OCH2CHCH2NH-C(CH3)3 with OH]

What is claimed is:

1. New compounds of formula:

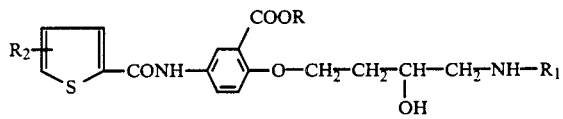

in which,

R represents an alkyl radical of 1 to 5 carbon atoms, straight or branched;

$R_1$ is an alkyl radical of 1 to 5 carbon atoms, straight or branched;

$R_2$ may be H, an alkyl radical of 1 to 5 carbon atoms, straight, branched or cyclic, or a halogen.

2. New compounds according to claim 1 selected from the group consisting of 1-[2-carbethoxy 4-(5-methyl 2-thiophene carboxamido)phenoxy]3-terbutylamino 2-propanol; 1-[2-carbethoxy 4-(5-methyl 2-thiophene carboxamido)phenoxy]3-isopropylamino 2-propanol; hydrochloride of 1-[2-carbethoxy 4-(5-chloro 2-thiophene carboxamido)phenoxy]3-terbutylamino 2-propanol; hydrochloride of 1-[2-carbethoxy 4-(4-methyl 2-thiophene carboxamido)phenoxy]3-terbutylamino 2-propanol; 1-[2-carbethoxy 4-(2-thienyl crboxamido)phenoxy]3-isopropyl amino 2-propanol; 1-[2-carbethoxy 4-(2-thienyl carboxamido)phenoxy]3-terbutyl amino 2-propanol and 1[2-carbomethoxy 4-(2-thienyl carboxamido)phenoxy]3-terbutylamino 2-propanol.

3. New compounds according to claim 1 wherein R is ethyl.

4. New compounds according to claim 1 wherein $R_1$ is isopropyl or terbutyl.

5. New compounds according to claim 1 wherein $R_2$ is hydrogen or methyl.

6. New compounds according to claim 1, wherein $R_2$ is cyclohexyl or cyclopentyl.

* * * * *

UNITED STATES PATENT AND TRADEMARK OFFICE
CERTIFICATE OF CORRECTION

PATENT NO. : 4,668,801
DATED : May 26, 1987
INVENTOR(S) : Jean M. Teulon and Etienne Bouley It is certified that error appears in the above-identified patent and that said Letters Patent is hereby corrected as shown below:

Title: front page and Column 1, change "30" to -- 3- -- and change "20" to -- 2- --;

Claim 2, Column 14, line 29, change "crboxamido" to

--carboxamido--.

Signed and Sealed this

Fifteenth Day of December, 1987

Attest:

DONALD J. QUIGG

Attesting Officer     Commissioner of Patents and Trademarks